United States Patent [19]

Blackwell

[11] Patent Number: 5,218,070
[45] Date of Patent: Jun. 8, 1993

[54] DENTAL/MEDICAL COMPOSITION AND USE

[75] Inventor: Gordon B. Blackwell, Konstanz, Fed. Rep. of Germany

[73] Assignee: Dentsply G.m.b.H., Konstanz, Fed. Rep. of Germany

[21] Appl. No.: 654,135

[22] Filed: Feb. 11, 1991

[51] Int. Cl.$^5$ .................. C08F 22/10; C08C 69/52
[52] U.S. Cl. .................. 526/318; 526/318.1; 526/318.2; 560/201; 560/198; 523/113
[58] Field of Search ........... 526/318.1, 318.2, 318; 523/113; 560/198, 201

[56] References Cited

U.S. PATENT DOCUMENTS

| | | | |
|---|---|---|---|
| 2,819,221 | 1/1958 | Smith | 560/198 |
| 4,400,531 | 8/1983 | Bush | 560/201 |
| 4,514,527 | 4/1985 | Bowen | 523/115 |
| 4,521,550 | 6/1985 | Bowen | 523/116 |
| 4,588,756 | 5/1986 | Bowen | 523/116 |
| 4,872,936 | 11/1989 | Engelbrecht | 156/307.3 |
| 4,964,911 | 11/1990 | Ibsen et al. | 106/35 |

FOREIGN PATENT DOCUMENTS

| | | | |
|---|---|---|---|
| 571111 | 2/1959 | Canada | 560/201 |
| 1123805 | 5/1989 | Japan . | |

OTHER PUBLICATIONS

Results of 2 literature searches. Relavent portions are highlighted by magic marker.

*Primary Examiner*—Paul R. Michl
*Assistant Examiner*—LaVonda R. DeWitt
*Attorney, Agent, or Firm*—Dale R. Lovercheck; Edward J. Hanson, Jr.

[57] ABSTRACT

The invention provides an improved dental/medical restorative/prosthetic composition employing a polymerizable unsaturated substituted butane moiety with acid or reactive acid derivative functionality having the general formula:

$$(RO_2C)_x\text{--}C_4H_6\text{--}(CO_2R')_y$$

where R is an acid radical or a reactive acid derivative and R' is a polymerizable unsaturated radical having from 2 to 13 C and x is 2 to 3 and y is 1 to 2.

27 Claims, No Drawings

DENTAL/MEDICAL COMPOSITION AND USE

The invention relates to a new class of dental/medical material based upon a relatively low molecular weight monomeric polymerizable unsaturated monomer of a substituted butane moiety with an acid or reactive acid derivative functionality.

BACKGROUND

U.S. Pat. No. 4,872,936 teaches dental cement mixtures containing polymerizable unsaturated monomers and/or oligomers and/or prepolymers containing acid groups and/or their reactive acid-derivative groups. However, the polymerizable compounds taught are directed toward those of relatively high molecular weight as compared to the very specific and advantageous specific class of compounds of the present invention. U.S. Pat. No. 4,589,756 relates to similar aromatic based compositions employed in dentistry.

By an aspect of the invention a new group of dental materials is provided that are kind to the patient, non-toxic and give superior adhesion to dentin, enamel and bone when properly formulated and that provide other favorable characteristics. The group of the preferred dental materials include especially cavity liner and bonding materials and filling materials.

The dental materials differ from earlier dental materials because they are based upon a new polymerizable composition system based upon a butane compound having in its preferred embodiments as primary preferred functional groups, olefins, more preferably (meth)acrylates and acid based radicals especially preferred is carboxylic acid and included are reactive acid derivative radicals. The butane (based) compound of this invention has the general formula:

$$(RO_2C)_x\text{—}C_4H_6\text{—}(CO_2R')_y$$

where is an acid radical or a reactive acid derivative and R' is a polymerizable unsaturated radical having from 2 to 13 C and x is 2 to 3 and y is 1 to 2.

OBJECTS

An object of this invention is the provision of new dental compositions useful as filling materials, cavity liners and bases, cements, pit and fissure sealants to prevent caries, as adhesive between tooth structure and/or bone and polymeric composites, and similar dental and orthopedic applications.

It is a further object to provide such dental/medical restoratives prosthetic compositions that have high purity, consistency and uniformity.

A further important object is to provide dental/medical restorative/prosthetic compositions that are relatively inexpensive and easy to manufacture.

Yet a further object of the invention is to provide dental/medical restorative/prosthetic compositions that are highly reactive and are relatively low viscosity fluid alleviating the need for high concentrations of diluents to provide suitable viscosity, thus giving superior dental/medical restoratives and prosthetics.

SUMMARY OF THE INVENTION

By the present invention in one aspect a new dental/medical restorative/prosthetic composition is provided that is based on a compound that is a polymerizable unsaturate substituted butane moiety with acid or reactive acid derivative functionality having the general formula:

$$(RO_2C)_x\text{—}C_4H_6\text{—}(CO_2R')_y$$

where R is an acid radical or a reactive acid derivative and R' is a polymerizable unsaturated radical having from 2 to 13 C and x is 2 to 3 and y is 1 to 2. The preferred compound is butane tetracarboxylic acid bis-(2-hydroxy ethylmethacrylate) ester. Preferably, the butane compound is the primary or only binder in the composition. By primary binder it is meant preferably in both quantity and functionality.

In one preferred aspect the composition is a dental liner consisting essentially of the butane compound and other active ingredients chosen from the group consisting of none, curing catalysts, initiators, accelerators and mixtures thereof. The dental liner in some preferred instances will contain other ingredients.

In another preferred aspect the composition is a dental composite comprising the butane compound, at least one finely divided reactive filler that can react ionically with the acids or acid derivative of the butane compound and curing agent.

By further aspects of the present invention the compositions recited above are employed for their recited purposes as dental treatments by application to teeth in vivo.

In yet other aspects the butane compound is employed as a medical treatment as an ingredient in bone cement and preferably as the primary or only binder in the bone cement.

BEST MODE

General Description

By an aspect of the invention new dental/medical restorative/prosthetic compositions are provided. These compositions are the product of the use of a class of compounds new to such use. As a liner or bonding agent, especially a dental liner for application to tooth enamel and dentin (meaning natural tooth structure), the compound can be applied in preferred forms neat or with only polymerization initiators added to assure quick curing and aid in completion of the cure of the compositions. Of course, depending on the application intended other materials may be added. When dental cements and composites are the intended compositions the compound of the present invention is used as a complete or a partial substitute for conventional resins.

The Chemical Compound Employed

The class of compounds that characterize the invention are those having as a principle functional ingredient polymerizable unsaturated monomers of a substituted butane moiety with acid or reactive acid derivative functionality having the general formula:

$$(RO_2C)_x\text{—}C_4H_6\text{—}(CO_2R')_y$$

where R is an acid radical or a reactive acid derivative and R' is a polymerizable unsaturated radical having from 2 to 13 C and x is 2 to 3 and y is 1 to 2. Preferably at least one carbon adjacent to each carbon carrying a $(CO_2R')_y$ is associated with a $(RO_2C)_x$ and the preferred polymerizable unsaturated radical is preferable a (meth)acrylate. (Meth)acrylate means either an acrylate or a methacrylate.

The compounds average molecular weight is preferably about 200–600, more preferable 260–499 and most preferably 290–460. The preferred compounds are liquid at room temperature. By liquid it is meant that the material is fluid with viscosities of less than 100,000 cps at 23° C.

The compounds essentially contain or include in a single chemical compound at least two different functional substituent groups, one of which is capable of addition polymerization and the other of which is carboxyl or other acid or reactive acid derivative. It is important that there be at least one such addition polymerizable group, but not more than two and there must be two or more acid or reactive acid derivative groups but in the most preferred compound there are no more than three. The preferred chemical compounds are in a preferred aspect derived from the reaction of butanetetracarboxylic acid or its anhydride with a hydroxyl or polyhydric compound to form esters and diesters.

The new dental/medical compositions of matter are capable of being polymerized to form linear or cross-linked polymers which contain multiple acid groups or reactive acid derivative groups that may be further reacted with cations, especially those of valence 2 or greater, to form poly-salts relatively insoluble in water. Because the compounds are monomers of relatively low molecular weight with a high density of both ethylenic unsaturation and carboxylic reactive acid derivative sites, excellent curing with superior integrity occurs. The cations may be supplied by ingredients or components of the given formulation or they may be supplied from a solution of cations supplied from a second component of the formulation, or they may be supplied from the substrate against which the formulation is polymerized especially the tooth in the preferred dental compositions where this provides an especially good bond in the preferred applications. In such a case the carboxyl ions, other acid ions or reactive acid derivative ions may be chelated with surface cations of the substrate to provide an adhesive bond. In a preferred dental composition not only is this substrate bonding available but bonding with an ion contributing inorganic filler aids in binding the entirety together. It will be understood that the term reactive acid derivative ions as used here includes the water soluble salts of cations, especially the monovalent species of cations, for example the sodium, ammonium and potassium salts, which are displaced by cations of greater valency by metathesis. However, the carboxyl group itself is most preferred over other acid groups or the reactive acid derivative ions. Especially appropriate acid groups are all those that can react with oxidic, mineral, ceramic, vitreous, or metallic fillers.

Examples of other acid radicals, the radicals include:

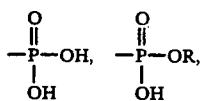

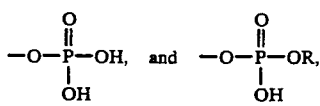

of phosphorus acids wherein R is alkyl, aryl, or vinyl for example, the radicals —SO$_2$H, SO$_3$H, OR —O—SO$_3$H of sulfuric acids, and the radicals

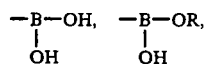

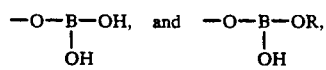

of boron acids wherein R is alkyl, aryl, or vinyl.

Cationic acid radicals like —NR$_2$H+ or —PR$_2$H+ (wherein R is H or alkyl) are also appropriate.

The reactive acid derivatives can be substituted with acid halides with acid anhydrides, and with acid amides, nitriles, and esters, that readily hydrolyze into acid, such can enter into ion-exchange, neutralization, salt formation, or chelation reactions with the reactive filler. Preferred are acid groups or reactive acid derivatives in the form of carboxylate, phosphate, phosphonate, sulfonate, or borate acid radicals or of their reactive derivatives.

Preferred polymerizable unsaturated radicals are alkenyl, alkenoxy, cycloalkenyl, radicals, with acryl, methacryl, vinyl, and of these, the olefins are preferred with the acrylic and methacrylic radicals being especially preferred.

For a better understanding of the characteristics and method of producing the preferred ethylenically unsaturated carboxylic acid compounds of the present invention the production of a most preferred series of the butane based compounds is described as follows showing a preferred method of their production:

For starting materials, Butane 1,2,3,4-tetracarboxylic acid is refluxed with acetic anhydride.

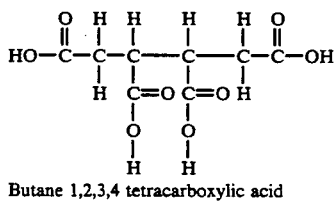

Butane 1,2,3,4 tetracarboxylic acid

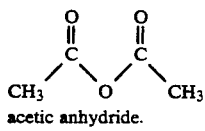

acetic anhydride.

The reaction yields butane tetracarboxylic acid di anhydride and acetic acid.

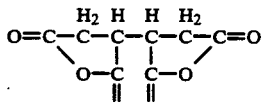

Butane tetracarboxylic acid anhydride

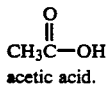

acetic acid.

One mole butane tetracarboxylic acid anhydride is then reacted with two moles 2-hydroxyethyl methacrylate (HEMA) in the presence of H$_2$SO$_4$ or other suitable catalyst.

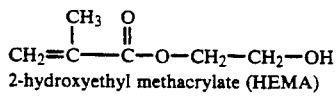
2-hydroxyethyl methacrylate (HEMA)

The reaction yields a liquid product, believed to be a mixture of isomer monomers of Butane tetracarboxylic acid bis (2-hydroxyethyl methacrylate) ester. The isomers differ in the positioning of the hydroxyethyl methacrylate moiety on the carboxylate groups.

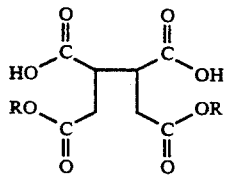

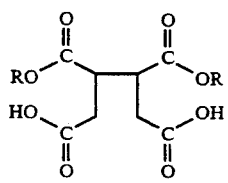

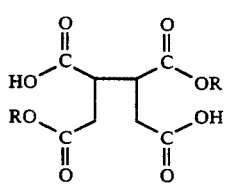

Butane tetracarboxylic acid bis (2-Hydroxyethyl methacrylate) esters.

In this example, R is the hydroxyethyl methacrylate moiety. Thus, the second isomer above would be structurally diagrammed as follows.

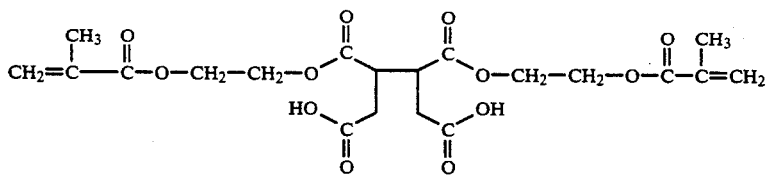

Butanetetracarboxylic acid bis (2-hydroxyethyl methacrylate) ester.

The Butane tetracarboxylic acid bis (2-hydroxyethyl methacrylate) esters are referred to by the initials BCA.

The above reaction gives a monomer molecule having two reacted carboxylic acid groups and two unreacted carboxylic acid groups. In an analogous manner 1 mole of butane-dicarboxylic-acid-anhydride may be reacted with 1 mole of hydroxy ethyl methacrylate to similarly yield isomers of butane tetracarboxylic acid mono (2-hydroxyethyl methacrylate). Different combinations of reactive esters may be formed by different concentrations of reactants; but according to the invention there must be at least two unreacted carboxylic acid group in the monomer. The number of reacted or unreacted carboxylic acid groups in the monomer is controlled by varying the reaction conditions.

The (meth)acrylate radical may be joined on in a number of ways, for example:

Exemplary radicals would be ethoxy acrylate

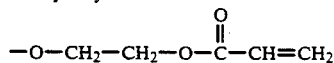

ethoxy methacrylate

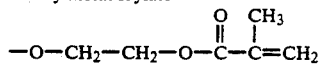

(iso) propoxy (meth)acrylate

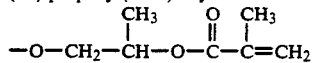

polyglycol methacrylate

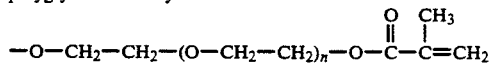

where n is preferably from 1 to 10.

amide

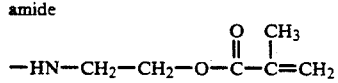

The preferred radicals would be the (meth) acrylates and especially the ethoxy (meth)acrylate radicals.

THE DENTAL/MEDICAL COMPOSITIONS

The compounds of this invention can desirably be used as primers in some preferred aspects with only initiators present or initiators and accelerators or only accelerators present. In some instances the butane compounds may be used neat or with only curing agents and ingredients that would be considered incidental and thus not counted when considering "consistency essentially of". Such incidental ingredients would be anti-oxidants, stabilizers and pigments and the like which may be included in proper instances.

The monomers of the present invention polymerize by well known addition polymerization procedures through the ethylenically unsaturated group by a variety of means. Most often curing agents, catalysts and initiators and accelerators, are used to expedite and control the polymerization. It is known in the dental art to practice addition polymerization by employing a peroxide, for example benzoyl peroxide, and heat to initiate the reaction. It is also known that accelerators enhance the reaction so that it may proceed more expeditiously at room temperature. Accelerators are reducing amines or sulfinates for example. It is also known to polymerize such compounds by ultraviolet and visible light using initiators and accelerators known to the art. Visible light curing is preferred. For preformed objects, or those cured outside the body, other forms of radiation, for example ionizing radiation is known.

It will be appreciated that in-vivo polymerization must take into account the suitability of the method and composition so as not to harm the patient within whom polymerization of the monomer or oligomer compound and the curing of the composition occurs. Thus the elements of a polymerization system, for example a peroxide and an amine, may be components of a two part formulation in which polymerization is delayed until the two parts are combined and react to polymerize the monomer. Or all the necessary chemical components may be combined within a single composition which is induced to polymerize by the application of heat or light or other initiating action. It is known for example to initiate by irradiation with ultraviolet or visible light in which case the initiator, often a benzophenone or camphoroquinone may be combined within a single, premixed, ready to use shelf-stable composition. A particular polymerization method and system may be preferred depending on the application requirements of the material. Whatever the mode of polymerization, or "cure" of the composition including the monomer or monomers an important characteristic of the polymers which form are that they are capable of further reaction with di- or polyvalent cations through their acid or reactive acid derivative functionality. A further important aspect of the compounds and compositions of the invention is that they exhibit adhesion between the monomer compound and a cation containing surface, metal, metal oxide, tooth bone and the like, against which they are polymerized.

One preferred class of compositions of the present invention are shelf-stable compositions that initiate curing in response to visible light. By shelf-stable it is meant the composition retains good application and curing characteristic when stored in a visible light opaque container at room temperature for one year or more. Curing by visible light refers to actinic light initiated compositions curing within the visible light range of approximately 360 to 600 nanometers.

In many dental and medical applications it is desirable to include fillers supplying reactive cations, and optionally non reactive fillers or mixtures thereof in the compositions of the present invention in preferred aspects thereof. Among those fillers which are especially suited for use in this invention are inorganic glasses such as are presently known in the art to form glass ionomer cement compositions. Exemplary of such fillers are those of U.S. Pat. No. 4,814,362 the contents of which are incorporated herein by reference. Preferred species of glasses include, for example, barium aluminosilicate, calcium aluminosilicate, and strontium, lanthanum, tantalum, tungsten, etc. glasses. Silica, including submicron silica, or quartz may also be used. Ceramic fillers, for example, calcium hydroxy apatite may also be used to good advantage. The fillers used in the invention may be reduced in particle size and then preferably silanated by methods known in the art before they are incorporated into such compositions. Preferred levels of filler material are from about 20% to about 80% based on the total weight of the adhesive composition, with from about 40% to about 70% being more preferable and about 45 to 60% being most preferred. If a more finely particulated filler is used, amounts of filler may be decreased due to the relative increase in surface area which attends the smaller sizes of particles. Preferred particle size distributions are from 0.02 to 50 microns, more preferably 0.1 to 10 microns, and most preferably 1 to 6 microns.

Other ingredients that may be present are, for example, solvents, plasticizers, pigments, anti microbials and therapeutics which may be time released from the composition and oxi-dation inhibitors such as butylated hydroxytoluene. The mixtures in accordance with the invention can also contain other polymerizable unsaturated monomers and/or oligomers and/or prepolymers that do not contain any acid groups and/or salts thereof and/or reactive readily hydrolyzing acid-derivative groups thereof. Particularly appropriate are monomers that are constituents of conventional composites such as for example hydroxy alkyl methacrylate. The mixtures can also if necessary contain other compounds that, although they contain acid groups and/or their salts and/or their reactive readily hydrolyzing derivative groups do not contain any groups that are unsaturated and polymerizable. Preferred in this case are multi-basic acids or their reactive, readily hydrolyzing derivatives. Especially preferred multibasic acids are hydroxy acids such as tartaric or citirc acid, but also polyacids such as polycarboxylic, polyphosphoric, polyphosphonic, or polysulfonic acids.

Compounds that have chelating groups but do not contain acid groups or readily hydrolyzing acid-derivative groups can be employed. Examples of this type are vanileates, syringates, and salicylates.

While one of the special advantages of the use of the class of compounds of the present invention in treating mammals, especially humans and especially in the maxiofacial, mouth area, in dentistry is the fact that the compounds are relatively fluid monomers and large amounts of diluents are not required, there are instances where diluents may be desirable. For example, in bonding agent adhesive compositions to aid in more completely and quickly wetting the substrate. Suitable diluents would be, for example, ethanol, water, and less viscous reactive monomers.

Mixing of the compositions of the present invention may be achieved using standard compounding techniques. for example, liquids, photoinitiator(s), and accelerator(s) are blended first, and then when fillers are to be included they are added incrementally thereafter. When blending light sensitive compositions, however, a photo-safe light, i.e., one that does not contain substantial amounts of wavelengths of electromagnetic radiation that would activate the photoinitiating system used, should be employed to avoid initiating polymerization prematurely.

The butane (based) compounds of the present invention also have medical applications, especially preferred would be the bone cements and adhesives. But the application of the present invention to dental treatment by application to a tooth or a number of teeth in vivo, in the mouth of a live patient by a dentist or dental practitioner, is a most preferred use.

One preferred dental treatment is the application of the composition as a dental liner. The dental liner composition may in one most preferred embodiment consist essentially of the butane compound and other active ingredients chosen from the group consisting of none, curing catalysts, initiators, accelerators, and mixtures thereof. In other preferred compositions diluents may be present or other ingredients may be present.

The composition is applied as a liner using conventional techniques and preferably cured with application of visible light in conventional manner. In other preferred embodiments the composition is a two-part system and the curing agent is spatuled in prior to placement and the placement is by standard technique. Yet another preferred embodiment is a comingation of the other two where there is a two-part system but after mixing the system is cured with visible light with substantial self-curing occurring.

Another preferred dental treatment is the application of the composition as a dental composite filling. The dental composite filling composition may in one most preferred embodiment consist essentially of the butane compound and other active ingredients chosen from the group consisting of finely divided reactive filler that can react ionically with the acids or acid derivative of said butane compound, curing agent and mixtures thereof. In other preferred compositions diluents may be present or other ingredients may be present.

The composition is applied as a composite filling using conventional techniques and preferably is a one-component composite filling material cured with application of visible light in conventional manner. In other preferred embodiments the composition is a two-part system and the curing agent is spatuled in prior to placement and the placement is by standard technique. Yet another preferred embodiment is a combination of the other two, where there is a two-part system but after mixing the system is cured with visible light with substantial self-curing occurring.

Having generally described the invention, a more complete understanding can be obtained with reference to certain specific examples, which are included for purposes of illustration only. It should be understood that the invention is not limited to the specific details of the Examples.

EXAMPLES

Throughout the Examples once a material, procedure or test procedure has been described, the description will not be repeated in subsequent Examples in most instances where the description remains the same, it being understood that the description applies in subsequent Examples. All ingredients are by weight unless otherwise specified.

METHOD FOR MEASUREMENT OF COMPRESSIVE STRENGTH

For each material to be tested, cylinders 4 mm diameter and 6 mm long were prepared by filling the mixed material into stainless steel molds and light curing from The each end for 40 seconds using a Prismetics TM light. The cylinders were removed from the molds and stored in water at 37° C. for 24 hours prior to testing. The force needed to load the specimens to breaking point was measured using a Zwick model 1455 set to a crosshead speed of 1 mm/min.

METHOD OF TRANSVERSE FLEXURAL STRENGTH

The uncured material was filled into a split stainless steel mold with internal dimensions 25 mm×2 mm×2 mm. The exposed faces were then covered with polyester foil and clamped between transparent plastic blocks approximately 5 mm thick. The material was light cured for a total of 120 seconds by moving a dental curing light evenly backwards and forwards along the mold with the wand of the light in contact with the plastic blocks. After curing, the hardened specimens were stored in water at 37° C. for 24 hours. Before being tested, any remaining flash along the edges of the specimens was carefully removed and the exact dimensions of each specimen measured. The specimens were then tested in three point bending mode using a Zwick model 1455 set to a crosshead speed of 1 mm/min, with the sample resting on supports 20 mm apart and being loaded at the mid point. The transverse bending strength was calculated from the standard formula in Mega Pascals (MPa).

METHOD FOR MEASUREMENT OF DIAMETRAL STRENGTH

For each material to be tested, cylinders approximately 6 mm diameter and 3 mm long were prepared by filling the mixed material into stainless steel molds and light curing from each end for 40 seconds using a Prismetics TM light. The cylinders were removed from the molds and stored in water at 37° C. for 24 hours prior to testing. Immediately before testing, the exact dimensions of each cylinder was measured with a micrometer, for use later in calculating the diametral strength. The force needed to load the specimens across the diameter to breaking point was measured using a Zwick model 1455 set to a crosshead speed of 10 mm/min.

BARCOL HARDNESS MEASUREMENTS

The Barcol hardness tester model GYZJ 935 was used for all measurements.

To avoid errors and effects due to changes in ambient lighting, these tests were carried out in a room with yellow lighting to which the photoinitiators systems are not sensitive. A circular brass mold having an internal diameter of 8 mm and a thickness of 1.3 mm was used. This was placed on a white surface and filled with the material to be tested. The surface was then covered with a small piece of transparent polyester film and the sample cured from above for the required time (usually 30 seconds), holding the end of the light guide lightly in contact with the foil. At the end of the curing time a stop watch was started and the hardness measured after 60 seconds.

It is necessary to wait 60 seconds after curing the materials and before measuring the hardness, since light cured compounds show a rapid increase in hardness during the first few seconds after curing, and attempts to measure during this time can lead to unnecessary variations and errors. A waiting period of sixty seconds was chosen since this could be reliably and reproducibly carried out, and the hardness of the compound is increasing relatively slowly at this time.

MEASUREMENT OF ADHESION TO DENTINE

Preparation of the Teeth

Extracted human teeth were cleaned and sterilized in 1% sodium hypochlorite solution. The teeth were then stored in fresh 1% sodium hypochlorite solution at 4° C. until needed. Both anterior and posterior teeth were used at random. Before use a dentine surface was exposed on each tooth by grinding an area of the crown flat with 300 grit abrasive paper, and then polishing this with 600 grit paper. All this work was carried out under water to avoid desiccation of the dentine.

PREPARATION OF ADHESION SAMPLES

Immediately before use, the prepared dentine surface was quickly blotted with a paper tissue. This removes excess surface water without drying out the tubules and the dentine retains its translucent appearance, rather than the white opaque appearance which occurs when excessive drying has taken place. A length of a plastic drinking straw approximately 4 mm long and 3 mm in diameter was then filled with the material to be tested, pressed lightly onto the dentine surface, and the material light cured through the straw for 40 seconds using a Prismetics ™ curing light. The prepared samples were normally tested after storage in water at 37° C. for 24 hours, though some were tested after only 10 minutes.

TESTING THE PREPARED SAMPLES

After storage for the required time, the samples were set in plaster so that the dentine surface was vertical. The samples were kept covered with a damp paper tissue during this time to avoid their desiccation. The force needed to shear the cylinders from the dentine was then measured using a Zwick model 1455 set to a crosshead speed of 1 mm/min, and the adhesion calculated in Mega Pascals.

Samples which were to be tested after 10 minutes were set in plaster before use.

PREPARATION OF POWDER SAMPLES

The ingredients were weighed into a glass bottle and thoroughly mixed by tumbling this for one hour. The powder was then passed twice through a 150μ nylon sieve before being transferred into a labeled container.

METHOD OF MEASURING FLUORIDE RELEASE

For each material, three cured discs having a diameter of 20 mm and a thickness of 1 mm were prepared. Each disc was placed into a bottle containing 25 ml of distilled water, and stored at 37° C. At intervals of one week the water was renewed, and the fluoride content of the old water determined in the presence of 10% TISAB IV buffer. The average measurement of the three discs was calculated and expressed in terms of μg fluoride ion per square cm of surface area of the disc (including the sides). Each week a blank was run by storing a bottle containing only water. The fluoride content of this was determined as a control. The electrode was calibrated before use using solutions with a known fluoride content, also in the presence of 10% TISAB IV buffer.

EXAMPLE 1

Preparation of Butane-1,2,3,4 tetracarboxylic dianhydride. (BTCA)

Butane-1,2,3,4 tetracarboxylic acid (230 g) (Aldrich-Chemie GmbH, catalog No. B,402-3, 97%) and acetic anhydride (690 ml) (Aldrich-Chemie GmbH, catalog No. 11,004-3, 99%) were placed in a 1500 ml flask fitted with a distillation fraction cutter and reflux condenser and heated with stirring to reflux for 3 hours. After this time, 250 ml of a mixture of acetic acid and acetic anhydride were slowly distilled out when the reflux temperature slowly increased from 118° C. to 138° C. The mixture was then stirred while it cooled. The crystals were filtered off using a suction funnel, washed twice with 300–400 ml of hexane, and the filter cake sucked dry. The white crystals (185 g) were then transferred to a desiccator and stored over sodium hydroxide pellets.

EXAMPLE 2

Preparation of Monomer A

Butane-1,2,3,4-tetracarboxylic acid, bis(2-hydroxyethyl methacrylate) ester is prepared as follows:

Butanetetracarboxylic acid dianhydride (34.5 g), 2-hydroxyethyl-methacrylate (HEMA, 50 g), (Aldrich-Chemi GmbH, catalog No. 12,813-5, 97%) and anhydrous sodium acetate (0.46 g) (Merk, catalog No. 6268), were stirred and heated together at 80° C. The changes in concentrations of reactants and products were followed by means of HPLC and IR spectroscopy, and after seven hours it was found that all the anhydride was consumed, and the reaction was therefore at an end. The product was a light colored viscous liquid, which was used directly in the formulations given elsewhere.

EXAMPLES 3 AND 4

Powder compositions were prepared from the following two ingredients:

*The Strontium glass was made according to U.S. Pat. No. 4,814,362 and had the following analysis with all elements except fluorine being calculated as the oxide of the element.

The mean particle size was 5.5 microns.

| Composition parts | |
|---|---|
| $SiO_2$ | 32.1 |
| $Al_2O_3$ | 24.6 |
| $Na_2O$ | 2.9 |
| SrO | 28.7 |
| F | 12.3 |
| $P_2O_5$ | 4.8 |
| polyacrylic acid (PAA) (molecular weight Specification range 30,000 to 45,000 Usual range around 35,000. | |

The powder was prepared by tumbling the glass and PAA together in a bottle for one hour, then passing the resultant mixture through a 150μ sieve. Two powder compositions, 3 and 4, were prepared as follows with the proportions given in parts by weight.

| Powder compositions | 2 | 3 |
|---|---|---|
| Strontium Glass | 90.9 | 80 |
| PAA | 9.1 | 20 |

EXAMPLES 5 to 10

Adhesive light cured Composition

A series of compositions were formulated from the ingredients in the proportions given in Table 1 in parts by weight.

Ingredients in given before
camphoroquinone (CQ) (Aldrich Chemical,GmbH catalog No. 23,122-3)
dimethaminobenzoic acid, ethyl ester (DMABE) (Aldrich Chemical, GmbH catalog No. E2,490-5)

The compositions were prepared by first mixing monomer A and 2-hydroxy ethylmethacrylate with stirring and then dissolving the camphoroquinone and dimethaminobenzoic acid, ethyl ester in the Monomer mixture with stirring at 50° C. Finally the water was added and stirred until totally dissolved. Roughly equal weights of the liquid and powder were mixed on a paper pad, when a fluid composition was obtained having a visually and tactually observed consistency suitable for use as a dental material, particularly as a lining material under fillings, as a cement, or as a fissure sealant. This was hardened by application of light from a dental curing light (Prismetics ® light, Dentsply International Inc.) for 30 seconds. The following properties were measured:

TABLE 1

| Examples | Liquid Components [in grams] | | | | | |
|---|---|---|---|---|---|---|
| | 5 | 6 | 7 | 8 | 9 | 10 |
| Monomer A | 6.25 | 7.14 | 6.82 | 6.00 | 4.50 | 8.50 |
| HEMA | 2.50 | 1.90 | 2.73 | 3.20 | 5.50 | 1.50 |
| Water | 1.25 | 0.95 | 0.45 | 0.80 | 0.00 | 0.00 |
| CQ | 0.06 | 0.06 | 0.06 | 0.06 | 0.06 | 0.06 |
| DMABE | 0.08 | 0.08 | 0.08 | 0.08 | 0.08 | 0.08 |
| Powder # | 2 | 2 | 2 | 2 | 3 | 3 |

The properties listed were evaluated with the results shown.

| | | | | | | |
|---|---|---|---|---|---|---|
| Barcol Hardness | 75 | 80 | 89 | 86 | 90 | 90 |
| Compressive Strength MPa | 62.1 | 72.4 | 91.4 | 81.2 | N/D | N/D* |
| Adhesion to wet Dentin MPa | 4.7 | 5.8 | 6.6 | 5.8 | N/D | N/D |
| Fluoride Release $\mu g/cm2$ | 17 | 31 | 40 | 34 | 92 | 60 |

These examples show the utility of the compositions as demonstrated by their strength, rapid polymerization, adhesion to wet dentin, and the ability to release fluoride from the glass component through the polymerized matrix of the compositions described.

EXAMPLE 11

| Powder Formulation | |
|---|---|
| Strontium Glass | 90 |
| PAA | 10 |
| Liquid Formulation | |
| Monomer A | 59.4 |
| 2-hydroxyethyl methacrylate | 31.8 |
| water | 8.0 |
| camphoroquinone | 0.38 |
| DMABE | 0.44 |
| Butylated hydroxytoluene | 0.01 |

The powder and liquid were mixed 1:1 [By weight] as in Examples 5 to 10. This gave a fluid cement like consistency suitable for use as a liner covering the floor of prepared dental cavities. Properties were determined and compared. The properties were compared to a commercial product, Vitra-bond ® a produce of 3M, sold for the stated purpose and also light polymerized.

TABLE 2

| | Example 11 | Vitrabond ® |
|---|---|---|
| Compressive Strength MPa | 81 ± 3.2 | 49 |
| Flexural Strength MPa | 17.2 ± 0.5 | 20.7 ± 1 |
| Flexural Modulus MPa | 1332 ± 252 | 1268 ± 115 |
| Diametral Tensile Strength MPa | 15.4 ± 0.9 | 17.6 ± 1 |
| Adhesion to wet dentin MPa | 8.4 ± 3.8 | 6.5 ± 1.3 |

| Barcol Hardness measured 60 seconds after irradiation for 30 seconds | | |
|---|---|---|
| Specimen Top Surface | 80 | 0 |
| Specimen Bottom Surface | 80 | 0 |
| Fluoride Release (7 days) $\mu g/cm2$ | 90 (7 days) | 114 (3 days) |
| Translucency C·.7 | clear | opaque |
| | <0.35 | >0.75 |

*measured using a Langer photometer model UME3.

EXAMPLE 12

Formulations of Monomer A with calcium glass.

| Powder Formulation | |
|---|---|
| Calcium Glass* | 75 |
| PAA | 25 |
| Liquid Formulation | |
| Monomer A | 59.4 |
| 2-hydroxyethyl methacrylate | 31.8 |
| water | 8.0 |
| camphoroquinone | 0.38 |
| DMABE | 0.44 |
| BHT | 0.10 |

*The Calcium glass had a mean particle size of 6.5 microns.

The powder and liquid were mixed 1:1 by weight on a paper pad as before. This gave a visible light curable (VLC) glass ionomer cement having a creamy consistency suitable for use, for example, as dental cavity liner or cement. It is believed that the glass provides calcium ion by elution which help to crosslink the polymerized mass. The mixture was cured by exposure to a dental curing light for 30 seconds irradiated from one surface only. The Barcol Hardness was 75 at the top surface and 70 at the lower surface 1.3 millimeters beneath the exposed surface.

The analysis was carried out at the Dorfner Analysen Zentrum, Hirschan, Germany.

| Composition by parts | |
|---|---|
| $SiO_2$ | 27.8 |
| $Al_2O_3$ | 31.3 |
| $Na_2O$ | 10.6 |
| CaO | 10.8 |
| F | 14.8 |
| $P_2O_5$ | 7.0 |

EXAMPLE 13

Formulations of Monomer A with calcium glass. Another powder was formulated as follows:

| Powder Formulation | |
|---|---|
| Calcium Glass | 85 |
| PAA | 15 |

The powder was combined with the liquid component of Example 12 at a ratio of 1:1 on a glass pad, and mixed with a dental spatula. As before, it was cured with a Prismetics light; the Barcol Hardness at the upper surface was 78 and the lower surface, 1.3 millimeters beneath, was 73.

Both Examples 12 and 13 show the ability of the monomers and compositions of the invention to be reactive and polymerize by addition polymerization in the presence of various glasses which provide cations capable of crosslinking the compositions. These ionically crosslinked polymers are useful as liners, cements and filling materials. They have exceptional translucency and may be cured to considerable depth compared to commercially available dental liners and cements.

EXAMPLE 14

Crosslinking with zinc oxide.

The liquid composition of Example 12 was combined on a dental mixing pad at a ratio of 1 part to 4.6 parts by weight of zinc oxide containing powder (Poly F TM Plus, DeTrey Dentsply, Konstanz) to form a stiff paste of a consistency suitable for use as a dental filling material. The powder contains 83% by weight of a zinc oxide mixture with minor amounts of the oxides of magnesium, aluminum and silica; 13% powdered polyacrylic acid, and 4% of tin fluoride. The surface of a mass of this material could be cured by 30 seconds exposure to a dental curing light to give a tough water resistant surface. Curing by irradiation with visible light was slower with this rather opaque composition than the composition of Example 12. The following table shows that the composition becomes cured whether or not exposed to light but that when polymerization occurs prior to crosslinking a hard composition results more rapidly, and that reaction with zinc oxide occurs even without prior polymerization. The composition has dental applications, for example, as a liner or base under permanent fillings, a temporary filling material, or as a cement.

TABLE 3

| Time (min) of Test | Barcol Hardness (test) | |
|---|---|---|
| | Light Cured | Not Light Cured |
| 0 | Light Cure 30 seconds | |
| 5 | 52 | 0 |
| 10 | 85 | 0 |
| 15 | 85 | 30 |
| 30 | 87 | 55 |
| 40 | 90 | 70 |
| 50 | 90 | 76 |
| 60 | 90 | 80 |

Readings were taken sequentially on one light cured and one non light cured specimen.

EXAMPLE 15

Tie Coat and Top Coat Compositions

The crown of an extracted human tooth was ground so as to expose a flat area of dentin. This was dried with a paper tissue and the liquid of Example 12 was applied in a thin layer. This was cured for 10 seconds with a Prismetics ® curing light used in standard clinical manner. A blob of the powder:liquid mixture of Example 39 was placed on top to cover an area about 4 mm in diameter. This was cured for 30 seconds with the Prismetics ® light used in the standard clinical manner. Five minutes later force was applied to the dentin composition interface using a metal spatula. It was not possible to dislodge the composition from the dentin surface by this means, indicating that its adhesion to dentin is at a high and clinically useful level. In contrast, a mixture of Poly F TM Plus powder (a composition formed by the combination of the same reactive zinc oxide filler and the same polyacrylic acid), and water which is the commercially recommended method for using this material, mixed according to directions and applied to a dentin surface, was easily dislodged.

These properties are especially valuable where rapid cure to good depth of inherently adhesive ionically crosslinked restorative materials are desired.

EXAMPLE 16 to 17

Preparation of Bonding Agents for Dental Composite Filling Materials

Formulations were made up as follows, where quantities are given in parts by weight.

| Ex. 16 | Monomer A | 52.59 |
|---|---|---|
| | HEMA | 38.49 |
| | water | 8.0 |
| | CQ | 0.38 |
| | DMABE | 0.44 |
| | BHT | 0.10 |
| Ex. 17 | Momomer A | 54.58 |
| | HEMA | 36.39 |
| | water | 3.99 |
| | 25% glutaraldehyde soln* | 3.99 |
| | CQ | 0.36 |
| | DMABE | 0.45 |
| | BHT | 0.23 |

*supplied by Fluka, catalog No. 49630

Adhesion of a composite material (AP.H TM, Dentsply International Inc.) to dentine was measured using the above liquid compositions as dentine primer or tie coat. The chosen liquid was brushed thinly onto the prepared dentine surface, and cured for ten seconds before applying the composite filled straw. The method was otherwise identical to the general method given before. Results are given below, and compared to those measured in a similar way for a commercially available dentine bonding agent (Prisma Universal Bond ®, Dentsply International Inc.).

TABLE 4

| liquid Ex. 16 | adhesion = 6.62 ± 2.09 MPa |
|---|---|
| liquid Ex. 17 | adhesion = 5.12 ± 1.86 MPa |
| dental bonding agent | adhesion = 4.22 ± 0.99 MPa |

Both experimental formulations therefore gave adhesion values at least as high as obtained with the commercially available material dental bonding agent (Prisma Universal Bond ® II), thereby demonstrating the usefulness of the monomer A in this application.

EXAMPLES 18 TO 21

Fluoride Ion Releasing Adhesive Formulations

Adhesive resin formulations were made up with compositions as shown below.

| liquid Ex. 18) | |
|---|---|
| Monomer A | 61.36 |
| 2-hydroxyethyl methacrylate | 3.39 |
| water | 4.51 |
| camphor quinone | 0.34 |
| DMABE | 0.40 |
| BHT | 0.1 |
| liquid Ex. 19) | |
| Monomer A | 51.15 |
| 2-hydroxyethyl methacrylate | 37.43 |
| water | 8.0 |
| camphor quinone | 0.38 |
| DMABE | 0.44 |
| BHT | 0.1 |
| Cetylamin hydrofluoride* | 2.5 |
| liquid Ex. 20) | |
| Monomer A | 51.15 |
| 2-hydroxyethyl methacrylate | 37.43 |
| camphor quinone | 0.38 |
| DMABE | 0.44 |
| BHT | 0.1 |

| | -continued | |
|---|---|---|
| Cetylamin hydrofluoride* (liquid Ex. 21) | | 2.5 |

*supplied by Merk, Germany, catalog No. 11679.

An attempt was made to formulate a composition containing an equivalent amount of fluoride ion using the composition of Ex. 18) but replacing the cetylamin fluoride with 0.2 parts of sodium fluoride. However, the sodium fluoride did not dissolve.

TABLE 5

| Bonding agent | Adhesion MPa | Fluoride release μg/cm² |
|---|---|---|
| liquid Ex. 18) | 6.62 ± 2.09 | 0 |
| liquid Ex. 19) | 4.39 ± 1.89 | 88 |
| liquid Ex. 20) | 2.73 ± 0.86 | 141 |
| Prisma Universal Bond ® II (Dentsply) | 4.22 ± 0.99 | 0 |

The adhesive is interesting in that the fluoride ions are totally dissolved in and dispersed evenly throughout the liquid, which remains glass clear when cured.

EXAMPLE 22

In order to further demonstrate the general usefulness of monomer A (the reaction product of butanetetracarboxylic acid dianhydride and 2-hydroxyethyl-methacrylate) as an adhesive agent or primer, a liquid composition was made up as follows.

1) Direct preparation of a solution of monomer A in HEMA

Butanetetracarboxylic acid dianhydride (500 g 2.5 moles), 2-hydroxyethylmethacrylate (1.5 kg 11.5 moles), BHT (1.5 g) and sodium acetate (5.0 g) were stirred and heated together at 80° C. for two hours, after which time a clear viscous liquid was obtained. The infrared spectrum of this showed that all the anhydride had reacted, and the reaction was therefore finished. The liquid, which consisted of a mixture of approximately 1500 grams of monomer A in approximately 850 grams of HEMA, was allowed to cool and used in the liquid formulation below.

2) Adhesive Primer composition in parts by weight

| solution of monomer A in HEMA | 200 |
|---|---|
| BHT | 0.44 |
| camphor quinone | 0.84 |
| DMABE | 0.97 |
| water | 17.59 |

The mixture was heated to 50° C., stirred until homogenous, then allowed to cool.

3) Use of the liquid composition in 2) as an adhesion primer to a nickel—chrome dental alloy.

Blocks of the metal alloy (Wiron 88, BEGO, Bremen, Germany) were prepared by grinding one surface flat on 220 grit silicon carbide paper. The surface was then rinsed under clean water and dried on a paper tissue. The liquid in 2) was brushed on thinly, and cured by exposure for 10 seconds to light from a Prismetics ® dental curing light. A section of a plastic drinking straw with an internal diameter of 5.25 mm and length of approximately 2 mm, was then held on the surface and filled with a commercially available composite material (AP.H. TM, Dentsply). This was cured by exposure to the Prismetics light for 40 seconds, after which the sample was stored in water at 37° C. for 24 hours. The shear bond strength was then tested in a Zwick model 1455 using a crosshead speed of 1 mm/min.

Using 6 samples, an average adhesion of 5.7±2.15 MPa was measured.

4) Adhesion to a cobalt—chrome alloy

The experiment in 3) was repeated using a cobalt—chrome alloy (Dentallium Extra hard, Svedia). A average adhesion of 7.3±1.7 MPa was measured for 7 samples.

5) Adhesion to Gold

A reclaimed gold crown was mounted on a steel post so that two faces could be held vertically in a clamp in the Zwick testing machine. The crown was cleaned well with a pumica/detergent mixture, rinsed well, and dried. The liquid from 2) was then brushed on in a thin layer, and cured for 10 seconds using a Prismetics light. AP.H. TM composite material was applied in a straw in the same way as for the previous examples, and cured for 40 seconds. The procedure was repeated for the other chosen face, and the crown stored in water at 37° C. for 15 minutes before the shear bond strength was tested in the Zwick machine at a crosshead speed of 1 mm/min.

For eight samples, an average shear bond strength of 6.2±2.6 MPa was measured.

6) Adhesion to ceramic material

Ceramic teeth (Dentsply GmbH, Dreieich, Germany) were sanded under water on 220 grit SiC paper to give a flat surface. The liquid from 2) was applied and cured, and AP.H. TM composite applied as in the previous examples. The prepared samples were then stored in water for 24 hours before being tested, again as in the previous examples.

In all samples failure was within the ceramic, so that after breakage large pieces of ceramic remained attached to the composite button. The true adhesion to ceramic was therefore not measured and the value of 8.53±3.93 MPa obtained is a measure of the strength of the ceramic teeth. However the highest value obtained was 15.2 MPa, indicating that adhesion is at a high and useful level, usually only obtained by silane treatment of the ceramic.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

What is claimed:

1. A dental/medical restorative/prosthetic composition comprising a polymerizable unsaturated substituted butane moiety with acid or reactive acid derivative functionality having the general formula:

$(RO_2C)_x\text{---}C_4H_6\text{---}(CO_2R')_y$ where R is hydrogen, an acid radical containing moiety or a moiety containing a reactive acid derivative and R' is a polymerizable unsaturated ester containing radical having from 2 to 13 C and x is 2 to 3 and y is 1 to 2.

2. The dental/medical restorative/prosthetic composition of claim 1 in the form of a dental liner or bonding agent consisting essentially of said butane compound and other active ingredients chosen from the group consisting of curing catalysts, initiators, accelerators and mixtures thereof.

3. The dental/medical restorative/prosthetic composition of claim 2 wherein said composition is one-component, system shelf-stable and visible light curable.

4. The dental/medical restorative/prosthetic composition of claim 1 in the form of a dental liner or bonding agent further comprising, curing agents and aldehyde.

5. The dental/medical restorative/prosthetic composition of claim 4 wherein said aldehyde is glutoraldehyde and said composition is one-component, system shelf-stable and visible light curable.

6. The dental/medical restorative/prosthetic composition of claim 1 in the form of a dental composite comprising said butane compound, at least one finely divided reactive filler that can react ionically with the acids or acid derivative of said butane compound and curing agent.

7. The dental/medical restorative/prosthetic composition of claim 1 in the form of a dental composite consisting essentially of said butane compound and other active ingredients chosen from the group consisting of finely divided filler which is ionically active with the acids or acid derivative of said butane compound, curing agent and mixtures thereof.

8. The dental/medical restorative/prosthetic composition of claim 1 in the form of a dental cement comprising curing agent and other ingredients chosen from the group consisting of finely divided filler which is ionically active with the acids or acid derivative of said butane compound, substantially nonionic filler, diluent and mixtures thereof.

9. The dental/medical restorative/prosthetic composition of claim 1 wherein said composition is a one-component system, shelf-stable and visible light curable.

10. The dental/medical restorative/prosthetic composition of claim 1 wherein R is H providing an acid radical CO(OH).

11. The dental/medical restorative/prosthetic composition of claim 1 wherein R is H and R' is a 2-hydroxyethylmethacrylate radical and x is 2 and y is 2.

12. The dental/medical restorative/prosthetic composition of claim 1 further comprising a inorganic particulate filler chosen from the group of glass, metal oxides, hydroxides, salts and mixtures thereof.

13. The dental/medical restorative/prosthetic composition of claim 12 wherein said filler is zinc oxide.

14. The dental/medical restorative/prosthetic composition of claim 1 further comprising a fluoride ion soluble in said composition.

15. The dental/medical restorative/prosthetic composition of claim 14 wherein said fluoride ions are amine fluorides.

16. The dental/medical restorative/prosthetic composition of claim 1 further comprising a fluoride ion eluting filler that is a source of cations reactive with said compound.

17. The dental/medical restorative/prosthetic composition of claim 1 in which said compound is butane tetracarboxylic acid bis-(2-hydroxyethylmethacrylate) ester.

18. A dental treatment comprising applying to a tooth in vivo a composition comprising a polymerizable unsaturated substituted butane moiety with acid or reactive acid derivative functionality having the general formula:

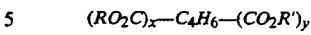

where R is hydrogen, an acid containing moiety or a moiety containing a reactive acid derivative and R' is a polymerizable unsaturated ester containing moiety having from 2 to 13 C and x is 2 to 3 and y is 1 to 2.

19. A dental treatment according to claim 18 wherein said treatment is the application of a dental liner or bonding agent and said composition consisting essentially of said butane compound and other active ingredients chosen from the group consisting of curing catalyst, initiators, accelerators, and mixtures thereof.

20. A dental treatment according to claim 18 wherein said treatment is the application of a dental composite and said composite comprises said butane compound, at least one finely divided filler ionically active with the acids or acid derivative of said butane compound and curing agent.

21. A dental treatment according to claim 20 further comprising fluoride ions applied as an ingredient of said composition.

22. A dental treatment according to claim 21 wherein said application involves direct application of the composition in its stored condition without mixing and curing is initiated with visible light.

23. A dental treatment according to claim 19 wherein said application involves direct application of the composition in its stored condition without mixing and curing is initiated with the application of visible light.

24. The composition of claim 1 wherein R is a hydroxyethyl methacrylate moiety.

25. The composition of claim 1 wherein R is ethoxy acrylate, ethoxy methacrylate, (iso) propoxy (meth) acrylate, or polyglycol methacrylate.

26. A dental/medical restorative/prosthetic composition comprising a polymerizable unsaturated substituted butane moiety with acid or reactive acid derivative functionality having the general formula

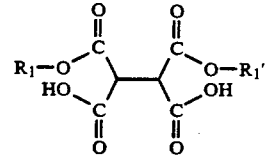

where $R_1$ and $R_1'$ independently are a moiety containing reactive acid derivative which is polymerizable, unsaturated and has from 2 to 13 carbons atoms.

27. The composition of claim 26 wherein $R_1$ is

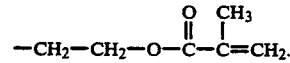

* * * * *